United States Patent [19]
Shibata et al.

[11] Patent Number: 5,102,527
[45] Date of Patent: Apr. 7, 1992

[54] CALCIUM ION SELECTIVE ELECTRODE

[75] Inventors: Yasuhisa Shibata, Oomiya; Naoto Oki, Hitachi, both of Japan

[73] Assignee: Hitachi, Ltd., Tokyo, Japan

[21] Appl. No.: 654,331

[22] Filed: Feb. 12, 1991

[30] Foreign Application Priority Data

Mar. 3, 1990 [JP] Japan .................. 2-52200

[51] Int. Cl.$^5$ .......................................... G01N 26/27
[52] U.S. Cl. .................... 204/416; 204/418
[58] Field of Search .............. 204/416, 418, 153.12, 204/153.2

[56] References Cited

U.S. PATENT DOCUMENTS

| | | | |
|---|---|---|---|
| 3,445,365 | 5/1969 | Ross | 204/417 |
| 3,932,233 | 1/1976 | Ruzicka et al. | 204/418 |
| 4,379,041 | 4/1983 | Petranek et al. | 204/418 |
| 4,437,969 | 3/1984 | Covington et al. | 204/416 |
| 4,519,891 | 5/1985 | Sugahara et al. | 204/418 |
| 4,713,165 | 12/1987 | Conover et al. | 204/416 |
| 4,814,060 | 3/1989 | Banks | 204/418 |
| 4,816,118 | 3/1989 | Oyama et al. | 204/418 |
| 4,874,499 | 10/1989 | Smith et al. | 204/416 |
| 4,889,612 | 12/1989 | Geist et al. | 204/416 |
| 4,929,313 | 5/1990 | Wrighton | 204/153.2 |
| 4,961,833 | 10/1990 | Sakai et al. | 204/416 |
| 4,981,570 | 1/1991 | Yamaguchi et al. | 204/418 |

*Primary Examiner*—John Niebling
*Assistant Examiner*—Bruce F. Bell
*Attorney, Agent, or Firm*—Fay, Sharpe, Beall, Fagan, Minnich & McKee

[57] ABSTRACT

A calcium ion selective electrode having a sensitive membrane comprising an organic polymeric substance, a plasticizer and a calcium ion sensitive substance of neutral carrier type, wherein the dielectric constant of the plasticizer is 10 or less, thus remarkably improving the responsiveness and stability of the electrode.

20 Claims, 6 Drawing Sheets

CALCIUM ION SELECTIVE ELECTRODE

BACKGROUND OF THE INVENTION

The present invention relates to a calcium ion selective electrode of a polymeric support membrane type suitable for the measurement of the concentration of a calcium ion in a living body fluid such as blood.

Ions which are cations contained in a living body fluid, particularly blood, and frequently measured in the field of clinical tests are sodium, potassium, lithium and calcium ions. Among them, the sodium ion which is contained in the highest concentration, having a normal value of concentration of 135 to 145 mmol/l.

On the other hand, the normal value of calcium ion concentration is 1 to 2 mmol/l, i.e., about two figures lower than that of the sodium ion. The measurement of the calcium ion has been regarded as clinically important for the diagnosis of thyroid gland function, never excitement and transfer function. From this point of view, it will be understood that whether or not the calcium ion can accurately be measured is an important key to the evaluation of the health condition based on the calcium ion concentration.

One of the methods of measuring the ion concentration of a living body fluid is an ion selective electrode method, and in recent years this method has come into wide use in the field of clinical tests. However, in order to realize an accurate measurement, it is necessary to eliminate a primary factor of error based on the influence of an interfering substance, etc., on the electrode.

If there is a coexistent ion, the relationship between the electrode output (E) and the activity (substantially equal to the concentration) when an intended ion is measured with an ion selective electrode can be expressed by the following equation (I):

$$E = E_0 + (RT/Z_iF) \log[a_i + \Sigma K_{ij}(a_j)^{z_i/z_j}] \quad (I)$$

where $E_0$ is the standard potential, R is the gas constant, T is the absolute temperature, F is the Faraday constant, a and z are the activity and valence of the intended ion (i) and the interfering ion (j), respectively, and $K_{ij}$ is the selectivity factor.

$RT/z_iF$ is called a slope sensitivity and serves as a measure of whether or not the ion selective electrode is satisfactory.

The slope sensitivity (29.58 mV/dec. at 25° C.) of a selective electrode (hereinafter referred to simply as the "electrode") which selects a calcium ion as a divalent ion and measures the ion concentration is one half of the slope sensitivity (59.16 mV/dec. at 25° C.) of an electrode for a sodium ion as a monovalent ion.

When the calcium ion concentration is measured by the ion selective electrode method, the selectivity of the electrode is lower than that of the electrode for the sodium ion and further as described above the concentration to be measured is very low, which makes it more difficult to conduct an accurate measurement.

An ion sensitive membrane is essential to the ion selective electrode. This sensitive membrane comprises a sensitive substance selectively responsive to the intended ion, a plasticizer which plasticizes and serves also as a solvent for the membrane, and a matrix material comprising a polymeric substance such as polyvinyl chloride. The characteristics of the electrode depend mainly upon the sensitive substance and plasticizer.

In order to realize an accurate measurement, it is necessary to:

(1) lower the selectivity factor, $K_{ij}$, of the ion selective electrode,
(2) present the interference by a lipophilic anion as shown in the equation (II) described later, and
(3) enhance the responsiveness of the electrode.

Although the selectivity factor described in the above item (1) is substantially determined by the ratio of the stability constant in a complex forming reaction of the sensitive substance with the intended ion, it essentially depends upon the sensitive substance. On the other hand, the properties of the plasticizer affect the interference by a lipophilic anion and the responsiveness of the electrode.

A neutral carrier and an ion exchanger have been used as the sensitive substance for the calcium ion selective electrode. When the sensitive substance is the former one, ether compounds, such as o-nitrophenyl octyl ether (dielectric constant $\approx 24$), have been used as the plasticizer [see Anal. chem. 1986, 58, 2282-2285 "Neutral Carrier Based $Ca^{2+}$—Selective Electrode with Detection Limit in the Sub-Nanomolar Range"], while when the sensitive substance is the latter one, plasticizers having relatively higher dielectric constants, such as esters of phosphoric acid such as di-n-octyl phenyl phosphate, have been used alone.

The present inventors have made various studies on the conventional ether compounds and other plasticizers in connection with the plasticizer for the sensitive membrane of a calcium ion selective electrode wherein use is made of a neutral carrier type of sensitive substance and, as a result, have found that a calcium ion selective electrode wherein use is made of a neutral carrier type of sensitive substance is susceptible to the interference by a lipophilic anion, with a different extent of influence depending also upon the plasticizer, and has a responsiveness susceptible to the properties of the plasticizer.

The above-described conventional sensitive membrane for a calcium ion selective electrode had problems with, for example, the sensitivity and responsiveness of the electrode.

SUMMARY OF THE INVENTION

An object of the present invention is to solve the above-described problems and to provide a calcium ion selective electrode which exhibits a high selectivity and excellent responsiveness and stability.

In order to attain the above-described object, the present invention provides a calcium ion selective electrode of a polymeric support membrane type having a sensitive membrane comprising an organic polymeric substance, a plasticizer and a calcium ion selective substance of neutral carrier type, wherein the dielectric constant of the plasticizer is 10 or less.

A plasticizer is essential to a sensitive membrane of an ion selective electrode. It plasticizes the sensitive membrane and serves also as a solvent for the membrane. According to the studies conducted by the present inventors, good results can be obtained when the dielectric constant of the plasticizer is 10 or less.

Examples of the plasticizer having a dielectric constant of 10 or less include esters of adipic acid, such as dioctyl adipate, bis(1-butylpentyl) adipate, bis (2-ethylhexyl) adipate and bis(1-butylpentyl)-decane-1,10-diyldiglutarate, dialkyl sebacates as esters of sebacic acid wherein the alkyl group has 4 to 8 carbon atoms, such as dioctyl sebacate, dibutyl sebacate, dihexyl sebacate and diheptyl sebacate, esters of phthalic acid having 4 to 8 carbon atoms, such as dibutyl phthalate, dipentyl phthalate and dioctyl phthalate, esters of phosphoric acid, such as tris(2-ethylhexyl) phosphate and dioctyl phenyl phosphate, and ether compounds such as diphenyl ether.

It is also possible to use alcohol compounds having 8 to 24 carbon atoms.

The above-described plasticizers may be used alone. When they are used in the form of a mixture, it is also possible to use plasticizers having a dielectric constant exceeding 10, such as o-nitrophenyl octyl ether, acetophenone and nitrobenzene. In this case, however, they should be mixed with plasticizers having a dielectric constant of 10 or less so that the dielectric constant value of the mixture is 10 or less.

It is desirable to add a salt of tetraphenylboric acid as an additive for preventing the interference by an anion. Examples of the salt of tetraphenylboric acid include sodium tetraphenylborate and potassium tetrakis-p-chlorophenylborate.

The calcium ion contained in an aqueous sample forms a cationic complex with a calcium ion sensitive substance and combines with a hydroxide ion or the like to form a ternary complex which is extracted into a sensitive membrane. On the other hand, when living body fluids, such as blood or urine, are measured, the use of a compound having a high dielectric constant as the plasticizer causes a lipophilic anion contained in a large amount if a living body fluid to combine as a counter ion of the cationic complex, which facilitates the distribution within the sensitive membrane.

The electromotive force (E) of the calcium ion selective electrode is expressed by the following equation:

$$E = E_0 + (1 - t_x) \cdot S \log(Ac) - t_x \cdot S' \log(Ax) \quad (II)$$

wherein $E_0$: standard potential,
$t_x$: transport number of anion,
$S, S'$: slope sensitivity,
$Ac$: calcium ion concentration, and
$Ax$: anion concentration.

When a lipophilic anion is distributed within a sensitive membrane, the third term of the equation (II) becomes nonnegligible even when the calcium ion is present in the same concentration, which causes the lipophilic anion to affect the electrode potential.

In view of the above, in order to decrease the influence of the lipophilic anion on the calcium ion selective electrode, measures should be taken to prevent the distribution of the lipophilic anion within the sensitive membrane. The plasticizer used for this purpose is preferably one having a low dielectric constant.

DETAILED DESCRIPTION OF THE PREFERRED EMBODIMENT

Figure 1:
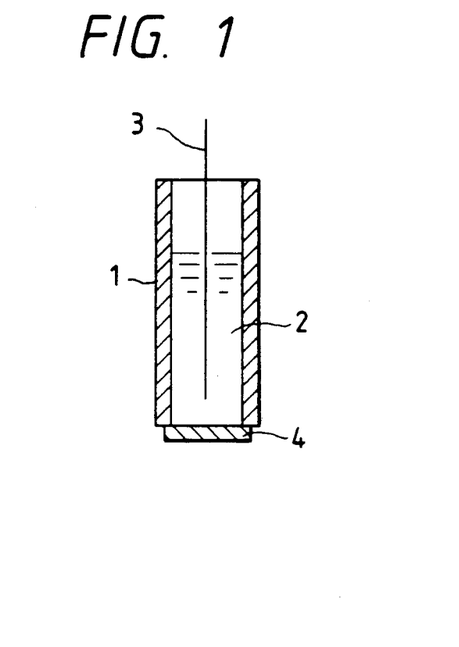
FIG. 1 is a cross-sectional view of the calcium ion selective electrode according to the present invention.

FIG. 1 is a cross-sectional view of one embodiment of the calcium ion selective electrode according to the present invention.

The form of the electrode is not limited to this only, and there is no particular limitation on the form of the electrode as far as use is made of a calcium ion sensitive membrane.

An electrode barrel 1 accommodates an internal solution 2 containing 10 mmol/l of calcium chloride, and an internal electrode 3 comprising silver/silver chloride is immersed in the internal solution 2. A sensitive membrane 4 is formed at the end of the electrode barrel 1. This sensitive membrane 4 comprises a polymeric substance, such as polyvinyl chloride, as a matrix material, and a calcium ion sensitive substance and a plasticizer and dispersed therein each in a suitable weight concentration.

Embodiment 1

1% by weight of [(−)-(R,R)—N,N'-bis[11-(ethoxycarbonyl)undecyl]-N,N'-4,5-tetramethyl-3,6-dioxaoctanediamide] (hereinafter referred to as "ligand A") as a calcium ion sensitive substance, 65.7% by weight of dioctyl sebacate (hereinafter referred to as "DOS"; dielectric constant: about 4) as a plasticizer, 33% by weight of polyvinyl chloride as a matrix material and 0.3% by weight of sodium tetraphenylborate as an additive for preventing the interference by cation were dissolved in tetrahydrofuran (THF). The resultant solution was cast within a glass ring having a diameter of 30 mm placed on a glass plate, and THF was evaporated to prepare a sensitive membrane of the present invention.

The above-described sensitive membrane was cut into a size of about 5 mm in diameter and bonded to the end of the electrode barrel 1 made from polyvinyl chloride to form a calcium ion selective electrode.

Figure 2:
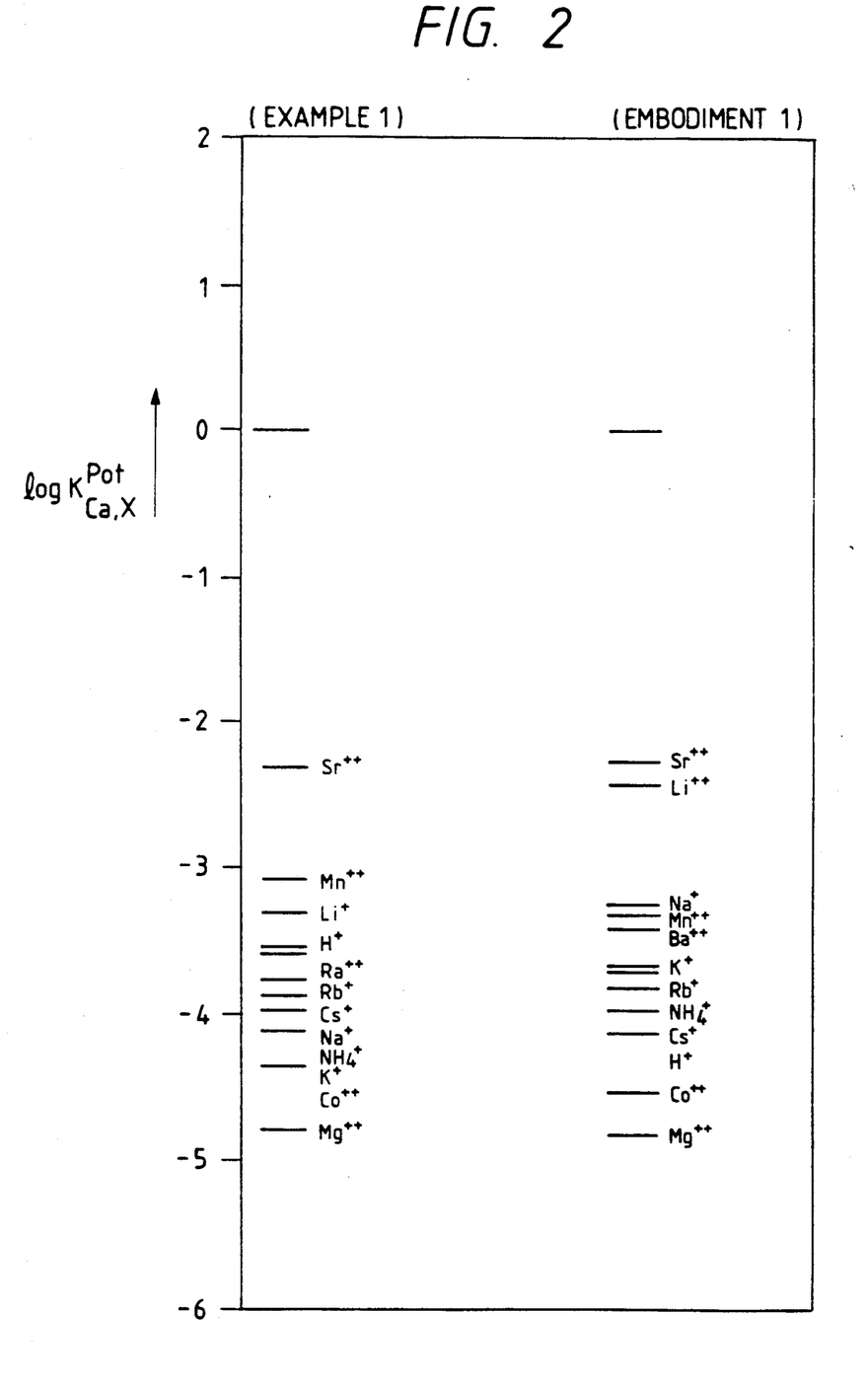
FIG. 2 is a graph showing the selectivity characteristics of the calcium ion selective electrode in Example 1 according to the present invention in comparison with those of the electrode in Comparison Example 1.
Figure 3A:
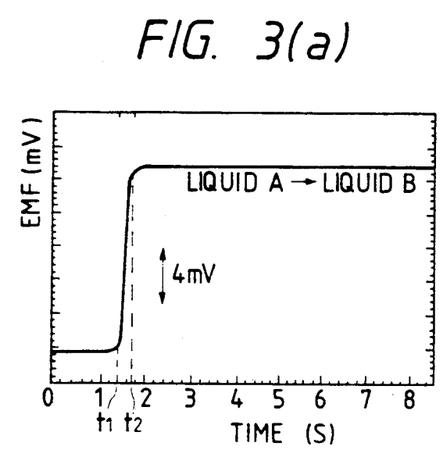
FIG. 3 is a graph showing the response characteristics of the calcium ion selective electrode in Example 1 (a,b) according to the present invention in comparison with those of the electrode in Comparison Example 1 (c,d)
Figure 3B:
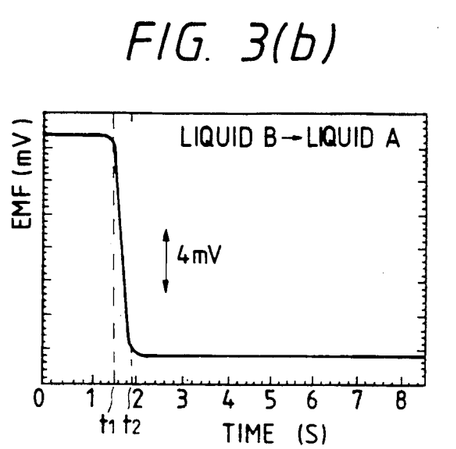
Figure 3C:
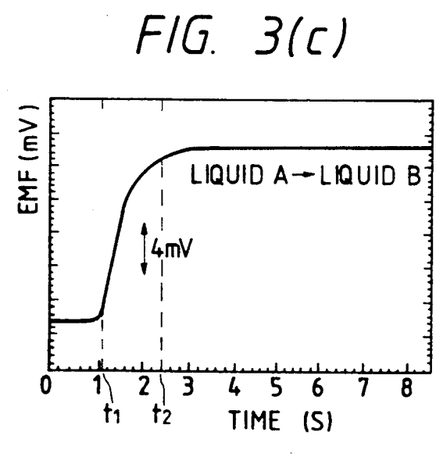
Figure 3D:
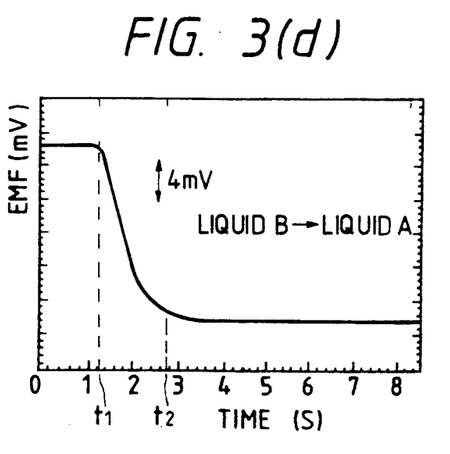

The selectivity for various ions was examined by the single solution method, and the results are given in FIG. 2.

EXAMPLE 1

A comparison was made on the performance of a calcium ion selective electrode having such an ion sensitive membrane composition such that only the plasticizer was different from that used in Embodiment 1.

The plasticizer used was o-nitrophenyl octyl ether having a relatively high dielectric constant (hereinafter referred to as "o-NPOE"; dielectric constant: about 24).

The calcium ion selective electrode was sufficiently conditioned with 10 mmol/l of an aqueous $CaCl_2$ solution, and the selectivity for various ions was examined by the single solution method according to JIS (K0122) to give the results of FIG. 2.

The selectivity in the Embodiment 1 was substantially the same as that in the Example 1, except for the sodium, potassium and lithium ions. When a living body fluid is a sample to be measured, it appears that judging from the ion concentration of said solution, the difference in the selectivity between the calcium ion-selective electrodes of the Embodiment and the Example has substantially no effect on the measurements.

Then, the responsiveness of the above-described calcium ion selective electrode was determined by the jet flow method.

The jet flow method is an effective method for determining the responsiveness inherent in an ion selective electrode.

When a sample solution is sprayed on the surface of a sensitive membrane of an ion selective electrode at a linear velocity of 200 to 300 cm/sec, the responsiveness inherent in the ion selective electrode can be obtained, because the thickness of the diffusion layer provided on the surface of the sensitive membrane is negligible. When the ion selective electrode is immersed in a solution, a concentration gradient occurs between the surface of the electrode membrane and the solution bulk. This is called a diffusion layer. If this diffusion layer is not negligible, a time taken for the ion to diffuse into the diffusion layer and reach the surface of the electrode is unfavorably added to the response time inherent in the ion selective electrode.

In order to make this diffusion layer negligible, there are a method wherein the solution is stirred by means of a stirrer, etc. and a jet flow method wherein the solution is sprayed on the surface of the ion selective electrode at a high velocity. The jet flow method is best suited when two solutions are used for determining the responsiveness.

A mixed solution (A) comprising 140 mmol/l of sodium ions, 5 mmol/l of potassium ions, 105 mmol/l of chloride ions and 2 mmol/l of calcium ions and a mixed solution (B) comprising 140 mmol/l of sodium ions, 5 mmol/l potassium ions, 150 mmol/l chloride ions and 5 mmol/l of calcium ions were alternately flowed at a linear velocity of 250 cm/sec to compare the respective response times with each other.

The response curves thus obtained are shown in FIGS. 3 (a) to (d).

The 95% response time (FIGS. 3 (a) and (b)) from the time $t_1$ to the time $t_2$ of the calcium ion selective electrode of Embodiment 1 was about 0.5 sec on the average (when measured five times).

On the other hand, the 95% response time (FIG. 3 (c) and (d)) from the time $t_1$ to the time $t_2$ of the calcium ion selective electrode of Example 1 was about 1.5 sec on the average (when measured five times). A significant difference exists between the responsiveness of both the electrodes, and it is apparent that DOS having a lower dielectric constant is more suitable for the plasticizer from the viewpoint of the responsiveness.

Embodiment 2

Use was made of the same calcium ion selective substance and matrix material as those of Embodiment 1, and dioctyl adipate (hereinafter referred to as "DOA"; dielectric constant: about 4) and potassium tetrakis-p-chlorophenylborate were added as the plasticizer and the additive for preventing the interference by an anion, respectively. The four raw materials for the sensitive membrane were used in a composition ration of 1.0% by weight, 64.0% by weight, 34.5% by weight and 0.5% by weight.

EXAMPLE 2

A comparison was made on the electrode performance through the use of the same calcium ion selective electrode as that of Example 2, except that o-NPOE was used as the plasticizer. The composition ratio of the four raw materials for the sensitive membrane was the same as that of Embodiment 2.

The selectivity for sodium ion and potassium ion is important in the measurement of the concentration of a calcium ion in a living body fluid. The selectivity for sodium ion was 0.0005 in the case of Embodiment 2 and 0.0001 in the case of Example 2. The selectivity for potassium ion was 0.0003 in the case of Embodiment 2 and 0.001 in the case of Example 2.

As with Embodiment 1, when o-NPOE was used as the plasticizer, the selectivity was slightly superior to the case where DOA was used as the plasticizer. However, the influence of the sodium ion or potassium ion in the living body fluid is one corresponding to that of the calcium ion of a concentration of 0.1 mmol/l or less, so that the difference in the selectivity between both of the electrodes brings about no problem from the viewpoint of practical use.

On the other hand, a difference in the response to a lipophilic anion ($SCN^-$ as an example) was observed between both the electrodes.

Two solutions (solutions C and D, respectively) prepared by adding each of $CaCl_2$ and $Ca(SCN)_2$ to a mixed solution comprising 140 mmol/l of sodium ions, 5 mmol/l of potassium ions and 105 mmol/l of chloride ions in a final concentration of 3 mmol/l. The results of the measurement conducted by respective calcium ion selective electrodes are given in Table 1.

Both of the calcium ion selective electrodes have substantially the same measured value with each other for solution C, while the measured values for solution D were different from each other.

It is apparent that the use of DOA as the plasticizer provides a more accurate measurement than that of the case where o-NPOE was used as the plasticizer.

The reason why the measured value for solution D was lower than the theoretical value even when use was made of DOA as the plasticizer resides in that part of $SCN^-$ combines with $CA^{2+}$ to thereby reduce the amount of calcium in the ionic form measurable by means of the calcium ion selective electrode.

TABLE 1

|  | Solution C | Solution D |
| --- | --- | --- |
| Embod. 2 | 2.97 mmol/l | 2.90 mmol/l |
| Embod. 3 | 2.95 mmol/l | 2.88 mmol/l |
| Ex. 2 | 2.96 mmol/l | 2.60 mmol/l |

The responsiveness of each of the calcium ion selective electrodes was determined by the jet flow method in the same manner as that of Embodiment 1.

Solutions A and B were alternately flowed at a linear velocity of 250 cm/sec to compare the response time.

The 95% response time of the calcium ion selective electrode of Embodiment 2 was about 0.4 sec on the average (when measured five times). On the other hand, the 95% response time of the calcium ion selective electrode of Example 2 was about 1.1 sec on the average (when measured five times). That is, a significant difference in the responsiveness was observed between both of the electrodes.

As is apparent from the relationship between the dielectric constant and the selectivity shown in FIG. 2, a plasticizer having a higher dielectric constant provides a higher selectivity but is influenced by the lipophilic anion to a greater extent, so that the use of a plasticizer having a smaller dielectric constant is preferred.

Embodiment 3

In the present Embodiment, the calcium ion sensitive substance, the additive and the matrix material were the same as those used in Embodiment 2, i.e., ligand A, potassium tetrakis-p-chlorophenyl-borate and polyvinyl chloride, respectively, and a mixture of DOA with o-NPOE (5:1) was used as the plasticizer.

The selectivity factor for sodium ion and potassium ion as determined by the single solution method were each 0.0001. The use of a mixed plasticizer rather than the single use of DOA as the plasticizer provided the same selectivity as that in the case where use was made of o-NPOE.

The measured values for solutions C and D are given in Table 1. As is apparent from Table 1, the results were substantially the same as those in the case of the single use of DOA.

Embodiment 4

In the present Embodiment N,N,N', N'-tetracyclohexyl-3-oxapentanediamide and tris (2-ethylhexyl) phosphate (dielectric constant: about 8) were used as the calcium ion sensitive substance and the plasticizer, respectively, and the additive, matrix material and concentrations thereof were the same as those of Embodiment 2.

The calcium ion selective electrodes of Embodiment 4 and Example 2 were immersed in 10 mmol/l of a $CaCl_2$ solution for one month or longer, and then subjected to the determination of the selectivity.

Figure 4:
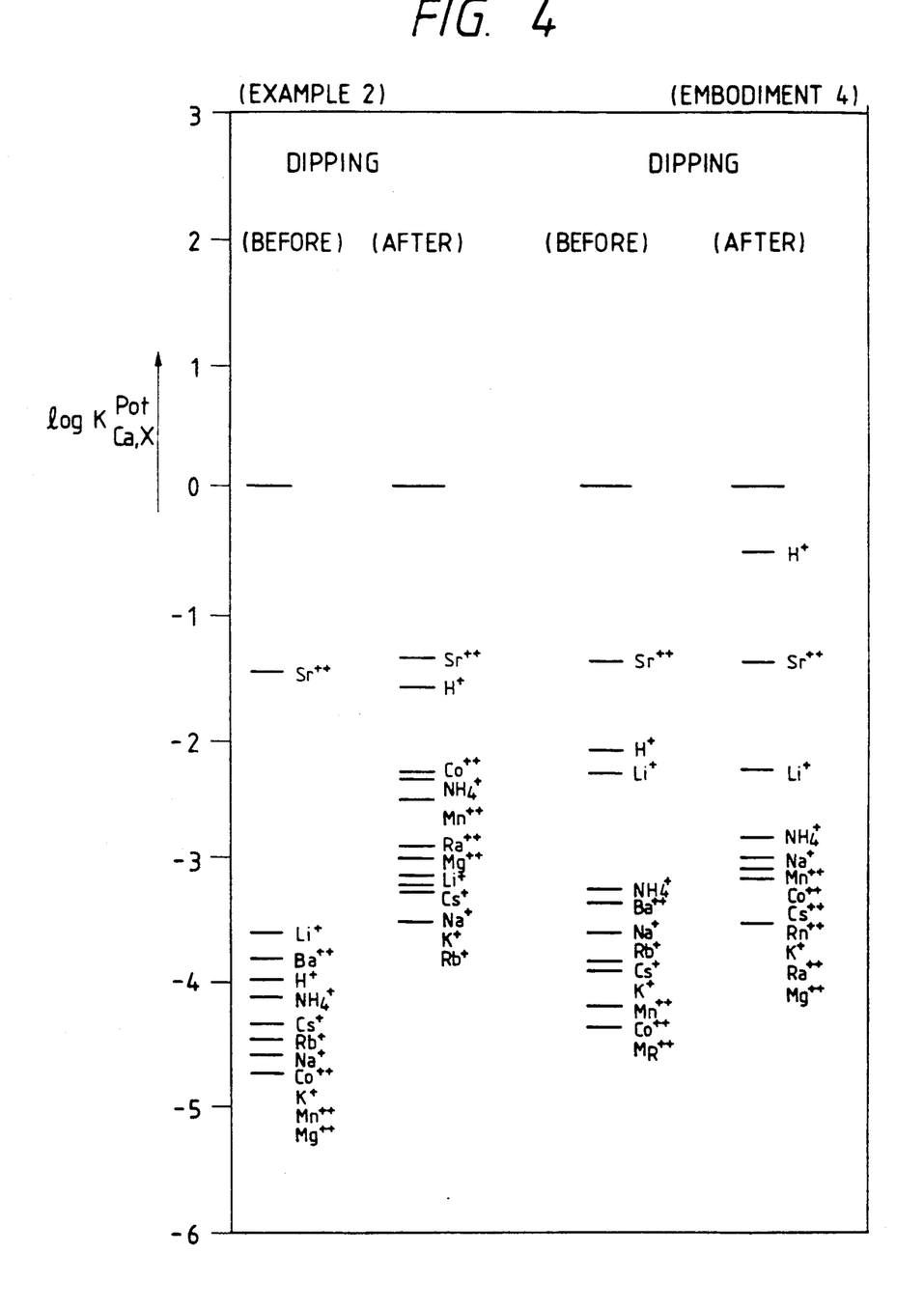
FIG. 4 is a graph showing the stability characteristics of the calcium ion selective electrode in Example 4 according to the present invention in comparison with those of the electrode in Comparison Example 2.

The results are shown in FIG. 4.

As is apparent from FIG. 4, although the selectivity varied in both the calcium ion electrodes, the extent of variation was smaller in the calcium ion selective electrode of Embodiment 4 and the use of a plasticizer having a lower dielectric constant provided a better stability.

Figure 5:
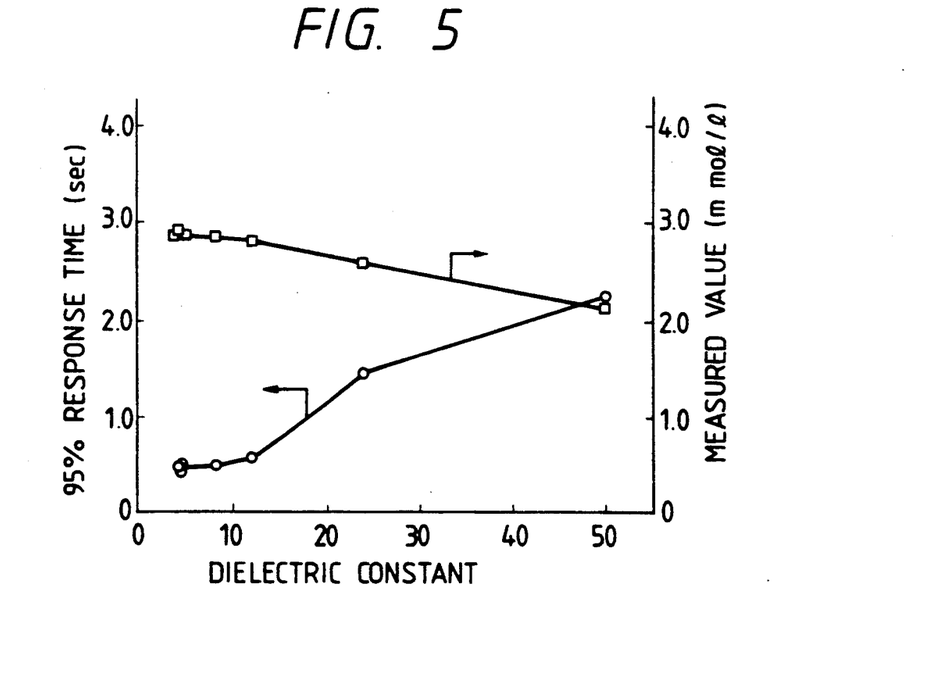
FIG. 5 is a graph showing the relationship between the characteristics of the calcium ion selective electrode according to the present invention and the dielectric constant of the plasticizer.

The relationship between the dielectric constant of plasticizers (single and mixed systems) and the 95% response time and the measured value for sample solution D of the calcium ion selective electrode as determined by the jet flow method is shown in FIG. 5.

When the dielectric constant exceeds 10, the 95% response time increases and the measured value for solution D begins to lower.

The lowering in the measured value for solution D is thought to be because the calcium ion selective electrode is influenced by a thiocyanate ion although the calcium ion concentration of the solution D is constant.

Figure 9:
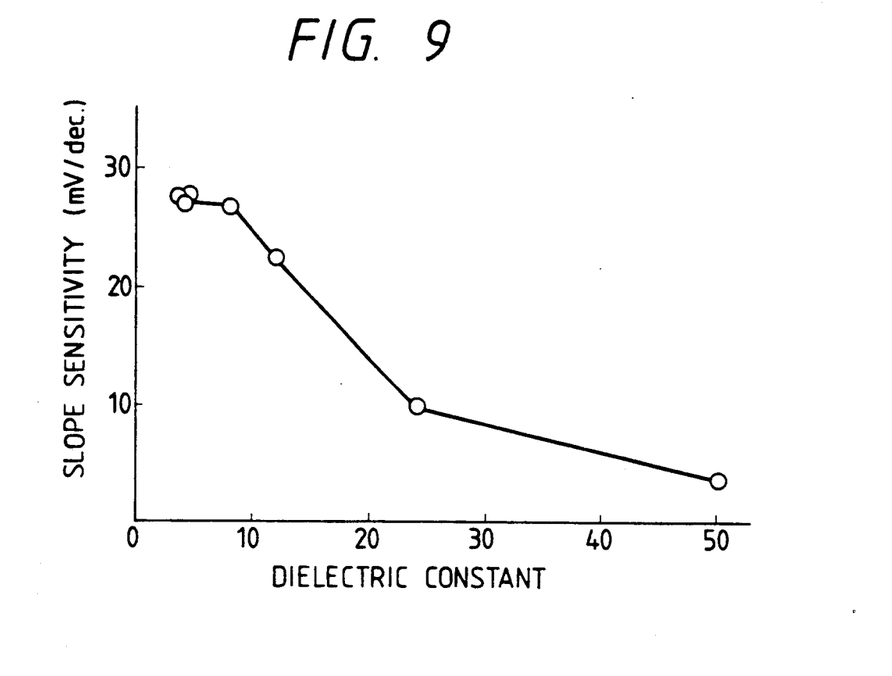
FIG. 9 is a graph showing the relationship between the dielectric constant and the slope sensitivity of the calcium ion selective electrode according to the present invention.

Further, the relationship between the dielectric constant of the plasticizer and the slope sensitivity is shown in FIG. 9. From this drawing, it is apparent that the slope sensitivity is high and the long-term stability is excellent when the dielectric constant is 10 or less.

As is apparent from the foregoing results, the dielectric constant of the plasticizer should preferably be 10 or less.

Embodiment 5

In the raw material composition of the ion sensitive membrane of Embodiment 2, the plasticizer was changed to 1-tetradecyl alcohol having a dielectric constant of 4.7.

The selectivity factor for sodium ion was 0.0005 as determined by the single solution method.

The above-mentioned alcohol compound should preferably be one having 8 to 24 carbon atoms from the viewpoint of preventing the deterioration of the calcium ion selective electrode caused by leaching from the sensitive membrane.

An alcohol compound having 25 or more carbon atoms is unfavorable because it precipitates in the sensitive membrane due to its high crystalline nature, which brings about a possibility of a lowering of the responsiveness of the calcium ion selective electrode or an increase of the electrode resistance.

Although a monohydric alcohol compound was used here, it is also possible to use a dihydric or higher alcohol compound.

Embodiment 6

A field-effect transistor was prepared through the use of the calcium ion sensitive membrane of Embodiment 2.

Figure 6:
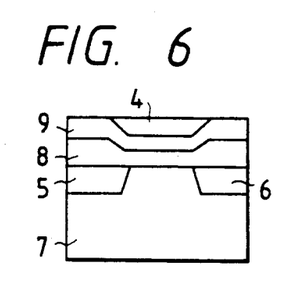
FIG. 6 is a cross-sectional view of a field-effect transistor for the measurement of a calcium ion according to the present invention.

FIG. 6 is a schematic cross-sectional view of the structure of the field-effect transistor.

An n-type source 5 and drain 6 were formed on a silicon substrate 7, and a $SiO_2$ film 8 and a $Si_3N_4$ insulating film 9 were formed thereon. Subsequently, the sensitive membrane 4 of Embodiment 2 was formed on the $Si_3N_4$ insulating film 9 to prepare a field-effect transistor 10 for the measurement of calcium ion.

Figure 7:
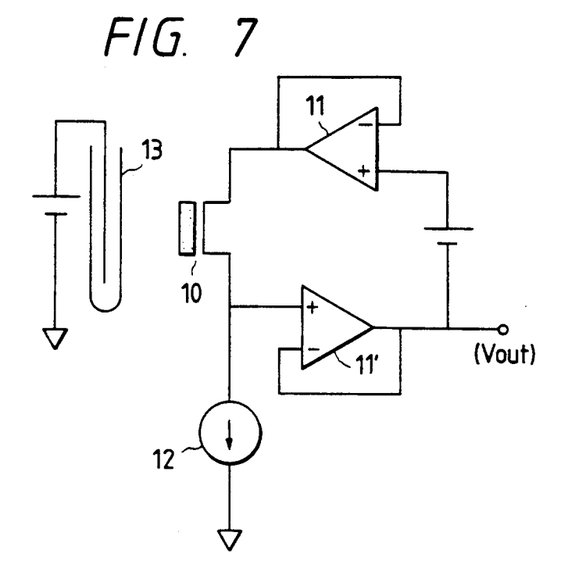
FIG. 7 is a circuit diagram for the measurement of a calcium ion wherein use is made of a field-effect transistor for the measurement of a calcium ion according to the present invention.

FIG. 7 is a circuit for measurement wherein use is made of the above-described transistor as a measuring circuit.

The transistor 10 is built in a measuring circuit comprising amplifiers 11 and 11', a constant-current power source 12, etc., and output (Vout) is effected through the use of the electrode in combination with a reference electrode 13 in a coupled form.

Embodiment 7

Figure 8:
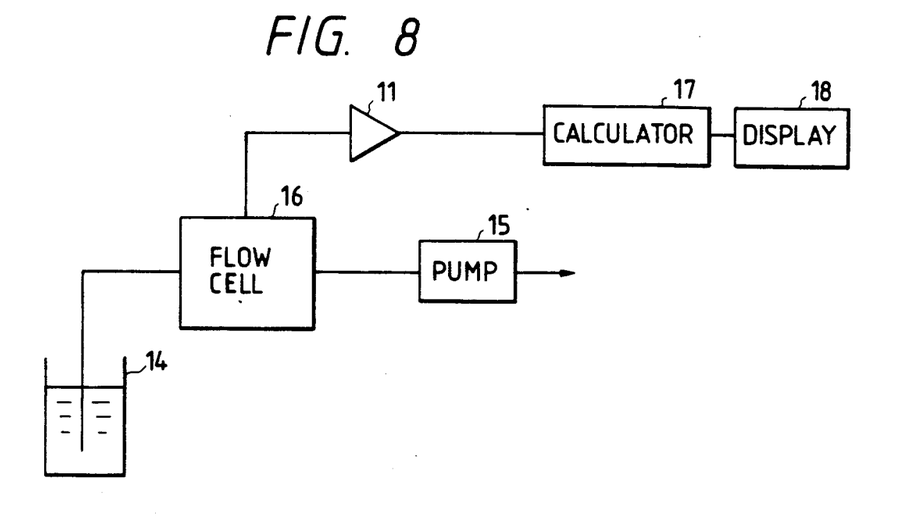
FIG. 8 is a block diagram of a living body fluid analyzer wherein the calcium ion selective electrode according to the present invention is used as a detector.

FIG. 8 is a block diagram of a living body fluid analyzer wherein a calcium ion selective electrode using the calcium ion sensitive membrane of the present invention was built as a detector.

A sample 14 for the measurement was sucked by means of a pump 15 into a flow cell 16 equipped with a calcium ion selective electrode and a reference electrode. An electromotive force corresponding to the calcium ion concentration occurs across the electrodes and amplified by means of the amplifier 11. Calculation is conducted by means of a calculator 17 based on the amplified signal, and the calcium ion concentration is displayed on a display 18.

It is also possible to use a living body analyzer for the measurement of a plurality of items wherein the ion selective electrodes for sodium and potassium ions were built as a detector, or gas electrodes, such as carbon dioxide electrode and oxygen electrode, were included in combination with the above-described ion selective electrodes.

It is also possible to use a measurement electrode of the field-effect transistor described in Embodiment 6.

The present Embodiment provides a living body fluid analyzer which exhibits a higher sensitivity than that of the conventional calcium ion selective electrode and excellent responsiveness and stability.

Embodiment 8

In the present Embodiment, the calcium ion sensitive substance, plasticizer, additive and matrix material were the same as those used in Embodiment 2, i.e., ligand A, dioctyl adipate (DOA), potassium tetrakis-p chlorophenylborate (hereinafter referred to as "KTpClPB") and PVC, respectively. The concentrations of the respective sensitive membrane materials were such that the PVC concentration was 34.5% by weight and the KTpClPB concentration was constant at 70% by mole based on the ligand A, while the concentration of the ligand A was varied from 0.5% by weight to 15% by weight. The balance was DOA as the plasticizer. A sensitive membrane was prepared in the above-described weight proportions, and the above-described calcium ion selective electrode was formed through the use of this sensitive membrane. The obtained calcium ion selective electrode were subjected to the measurement of the initial slope sensitivity and the selectivity factor for coexistent ions and then immersed in the serum to determine the variation of the electrode characteristics with time. For comparison, calcium ion selective electrodes equipped with the same sensitive membranes as those of the present Embodiment except for the variation in the concentration of ligand A from 0.5% by weight to 15% by weight with the use of o-NPOE as the plasticizer were immersed in the serum for the measurement of electrode characteristics in the same manner as that of the present Embodiment. As a result, it has been found in the Example that the immersion of the calcium ion selective electrodes in the serum for 5 days causes the slope sensitivity to rapidly lower from the initial value of 25 mV/dec. to 19 mV/dec. in all of the calcium ion selective electrodes, which renders the calcium ion selective electrodes substantially unusable. By contrast, the calcium ion selective electrode equipped with the sensitive membrane of the present Embodiment wherein use was made of DOA as the plasticizer had the same slope sensitivity as the initial value of 25 mV/dec. or more, that is, the electrode was stable, even after the serum immersion test for about 20 days. Therefore calcium ion selective electrodes were prepared while varying the dielectric constant of the plasticizer to confirm that the initial slope sensitivity was 25 to 27 mV/dec, and the electrodes were immersed in 10 mmol/l of an aqueous calcium chloride solution for three weeks. As a result, no significant variation of the slope sensitivity was observed relative to the initial value. On the other hand, the immersion of the electrode in the serum for five days followed by the determination of the slope sensitivity in the same manner as that described above gave the results shown in FIG. 9. Namely it has become apparent that the higher the dielectric constant of the plasticizer, particularly when the dielectric constant is 10 or higher, the more rapid the lowering in the slope sensitivity and the poorer the stability. Thus, it has been found that the calcium ion selective electrode wherein use is made of a plasticizer having a high dielectric constant has a substantially short electrode life. This is thought to be because when the dielectric constant of the plasticizer is high, the electrode is susceptible to the adsorption of proteins contained in the serum.

Figure 10:
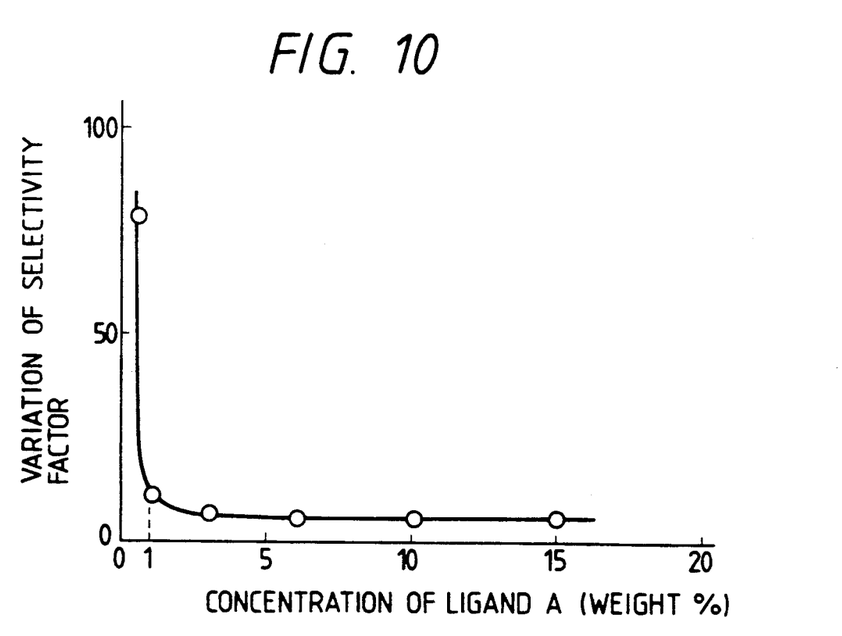
FIG. 10 is a graph showing the relationship between the ligand concentration and the variation of the selectivity factor of the calcium ion selective electrode according to the present invention.

Next the calcium ion selective electrode of the present Embodiment was immersed in the serum to determine the variation with time of the selectivity factor for sodium ion which is a cation present in the largest amount in the blood, and the results are shown in FIG. 10. The abscissa represents the concentration of ligand A, while the ordinates represents the ratio of the selectivity factor for sodium ion after the immersion of the electrode in the serum for 20 days to the selectivity factor for sodium ion before the immersion. The larger the value, the larger the variation of the selectivity factor for sodium ion. It has been found that the variation of the selectivity factor for sodium ion in the case of the immersion of the electrode in the serum tends to vary depending upon the concentration of the calcium ion sensitive substance. Specifically, an observed tendency is that the variation of the selectivity factor for sodium ion reduces as the concentration of ligand A increases. From the above results, it is apparent that in order to stably maintain the characteristics of the calcium ion selective electrode for a long period of time, it is effective to use a plasticizer having a low dielectric constant and, at the same time, to set the concentration of the calcium ion sensitive substance at 1 to 15%. However, since the ion sensitive substance is generally expensive, the concentration of the calcium ion sensitive substance is thought to be preferably 3 to 10% from the viewpoint of the electrode characteristics and profitability. In view of the above-described results, a calcium ion selective electrode as one example equipped with a sensitive membrane comprising 6.0% by weight of ligand A, 56.5% by weight of DOA, 3.0% by weight of KTpClpB and 34.5% by weight of PVC was used for the measurement on a blood sample by the non-dilution method. As a result, the slope sensitivity of the calcium ion selective electrode was found to be substantially the same as the initial value of 27 mV/dec. even after the measurement of 6000 specimens of a blood sample. The selectivity factor for sodium ion was $3 \times 10^{-4}$.

As described above, the calcium ion sensitive membrane of the present invention can provide a calcium ion selective electrode having a high reliability and a living body fluid analyzer using said electrode by virtue of its high sensitivity and excellent stability and responsiveness.

What is claimed is:

1. A calcium ion selective electrode having a sensitive membrane comprising an organic polymeric substance, a plasticizer and a calcium ion sensitive substance of neutral carrier type,
   wherein the effective dielectric constant of the plasticizer is 10 or less.

2. A calcium ion selective electrode as claimed in claim 1, wherein said plasticizer is an organic compound selected from the group consisting of ester compounds, ether compounds and alcohol compounds having 8 to 24 carbon atoms.

3. A calcium ion selective electrode having a sensitive membrane comprising an organic polymeric substance, a plasticizer and a calcium ion sensitive substance of neutral carrier type,
   wherein said plasticizer is selected from the group consisting of esters of adipic acid, esters of sebacic acid, esters of phthalic acid, esters of phosphoric acid and compounds represented by the formula X—O—X', wherein X and X' are each selected from the group consisting of an alkyl group, a phenyl group and its derivative.

4. A calcium ion selective electrode according to claim 1, which further comprises a salt of tetraphenylboric acid wherein the phenyl group may be substituted.

5. A field-effect transistor for the measurement of calcium ion, comprising a silicon substrate and, formed thereon, an n-type source and drain and, further formed thereon, a $SiO_2$ film and a $Si_3N_4$ insulating film,
   wherein a sensitive membrane comprising an organic polymeric substance, a plasticizer and a calcium ion sensitive substance of neutral carrier type is provided at least on said $Si_3N_4$ insulating film; and wherein said plasticizer has an effective dielectric constant of 10 or less.

6. A calcium ion selective electrode according to claim 1, wherein said sensitive membrane further comprises a salt of tetraphenylboric acid and said calcium ion sensitive substance has a concentration of 1 to 15% by weight.

7. A calcium ion selective electrode according to claim 2, which further comprises a salt of tetraphenylboric acid where the phenyl group may be substituted.

8. A calcium ion selective electrode according to claim 3, which further comprises a salt of tetraphenylboric acid wherein the phenyl group may be substituted.

9. A calcium ion selective electrode according to claim 2, wherein said sensitive membrane further comprises a salt of tetraphenylboric acid and said calcium ion sensitive substance has a concentration of 1 to 15% by weight.

10. A calcium ion selective electrode according to claim 3, wherein said sensitive membrane further comprises a salt of tetraphenylboric acid and said calcium ion sensitive substance has a concentration of 1 to 15% by weight.

11. A calcium ion selective electrode according to claim 4, wherein said sensitive membrane further comprises a salt of tetraphenylboric acid and said calcium ion sensitive substance has a concentration of 1 to 15% by weight.

12. A calcium ion selective electrode as claimed in claim 1, wherein the plasticizer comprises first and second plasticizer compounds having a ratio of 5:1 by weight.

13. A calcium ion selective electrode as claimed in claim 3, wherein the plasticizer comprises first and second plasticizer compounds having a ratio of 5:1 by weight.

14. A field-effect transistor as claimed in claim 5, wherein the plasticizer comprises first and second plasticizer compounds having a ratio of 5:1 by weight.

15. A calcium ion selective electrode as claimed in claim 2, wherein the alcohol compounds are monohydric alcohol compounds.

16. A calcium ion selective electrode as claimed in claim 2, wherein the alcohol compounds are polyhydric compounds.

17. A calcium ion selective electrode as claimed in claim 6, wherein said calcium ion sensitive substance has a concentration of 3 to 10% by weight.

18. A calcium ion selective electrode as claimed in claim 9, wherein said calcium ion sensitive substance has a concentration of 3 to 10% by weight.

19. A calcium ion selective electrode as claimed in claim 10, wherein said calcium ion sensitive substance has a concentration of 3 to 10% by weight.

20. A calcium ion selective electrode as claimed in claim 11, wherein said calcium ion sensitive substance has a concentration of 3 to 10% by weight.

* * * * *